United States Patent [19]

Nagarajan

[11] 4,145,538
[45] Mar. 20, 1979

[54] 3-CARBAMYLOXYMETHYL-CEPHALOSPORINS

[75] Inventor: Ramakrishnan Nagarajan, Indianapolis, Ind.

[73] Assignee: Eli Lilly and Company, Indianapolis, Ind.

[21] Appl. No.: 831,324

[22] Filed: Sep. 7, 1977

Related U.S. Application Data

[60] Continuation of Ser. No. 683,984, May 6, 1976, abandoned, which is a division of Ser. No. 374,222, Jun. 27, 1973, abandoned, which is a division of Ser. No. 139,913, May 3, 1971, abandoned.

[51] Int. Cl.$^2$ .................................... C07D 501/60
[52] U.S. Cl. ..................... 544/16; 544/22; 544/23
[58] Field of Search .................. 544/16, 29, 22, 23

[56] References Cited

U.S. PATENT DOCUMENTS

| 839,100 | 12/1906 | Bischler | 260/482 |
|---|---|---|---|
| 3,660,395 | 5/1972 | Wright et al. | 260/243 C |
| 3,660,396 | 5/1972 | Wright | 260/243 C |
| 3,668,201 | 6/1972 | Gutowski | 260/243 C |
| 3,668,202 | 6/1972 | Foster et al. | 260/243 C |
| 3,673,183 | 6/1972 | Erickson | 260/243 C |
| 3,674,775 | 7/1972 | Spry | 260/243 C |
| 3,674,784 | 7/1972 | Webber | 260/243 C |
| 3,694,437 | 9/1972 | Jackson | 260/243 C |
| 3,706,746 | 12/1972 | Bosshardt et al. | 260/243 C |

OTHER PUBLICATIONS

Fieser et al., Reagents for Organic Synthesis, pp. 117 and 1219 (1967).
Hedin et al., Analytical Chemistry, vol. 42, No. 3, pp. 403-406, Mar. 1970.

*Primary Examiner*—Jose Tovar
*Attorney, Agent, or Firm*—Kathleen R. S Page; Everet F. Smith

[57] ABSTRACT

The present invention is directed to 7-amino-3-carbamoyloxymethyl-3-cephem-4-carboxylic acid:

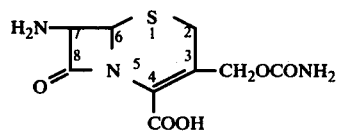

and to precursors and derivatives. The compound, its precursors, and its derivatives exhibit antibacterial activity, which, in the instance of certain of the derivatives, is of an enhanced degree.

5 Claims, No Drawings

3-CARBAMYLOXYMETHYL-CEPHALOSPORINS

This is a continuation, of application Ser. No. 683,984, filed May 6, 1976, now abandoned which was a division of Ser. No. 374,222 filed June 27, 1973, now abandoned which was in turn a division of then copending application Ser. No. 139,913, filed May 3, 1971, and abandoned after the filing of application Ser. No. 374,222.

BACKGROUND OF THE INVENTION

The cephalosporins are a well-known family of antibiotics. Cephalosporin C, the only member of the family produced by fermentation:

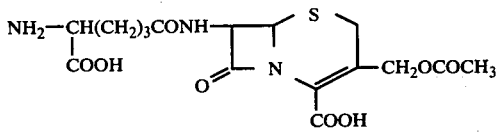

is of only a relatively low order of activity, and hence structural modifications have been made to convert it to more active family members. Typically, the "α-aminoadipoyl" side chain is removed to obtain 7-aminocephalosporanic acid ("7-ACA") which is then reacylated. In addition, structural modifications have been made at the 3-position. Belgian Pat. No. 741,381, for example, describes a class of cephalosporin compounds bearing on the 3-position, inter alia, a carbamoyloxymethyl moiety. However, the patent expressly teaches and exemplifies only substituted carbamoyloxymethyl moieties; the patent does not teach a method useful to obtain an unsubstituted carbamoyloxymethyl moiety.

SUMMARY OF THE INVENTION

The present invention is directed toward cephalosporin "nucleus" compounds bearing an unsubstituted 3-carbamoyloxymethyl moiety:

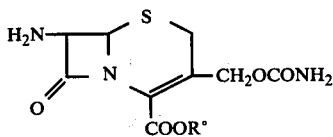

and to precursors of these compounds. In the above and succeeding formulae, $R°$ represents hydrogen or $R^1$, and $R^1$ represents alkyl of $C_1-C_6$, 2,2,2-trichloroethyl, 2-iodoethyl, tert-alkenyl of $C_5-C_7$, tert-alkynyl of $C_5-C_7$, benzyl, nitrobenzyl, tetrahydropyranyl, succinimidomethyl, phthalimidomethyl, methoxybenzyl, dimethoxybenzyl, cyanomethyl, nitrophenyl, dinitrophenyl, 2,4,6-trinitrophenyl, bis(p-methoxyphenyl)methyl, triphenylmethyl, diphenylmethyl, benzyloxymethyl, loweralkanoyloxymethyl of $C_3-C_6$, phenacyl, loweralkanoyl of $C_2-C_4$, or radical of the formula

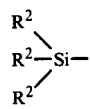

wherein each $R^2$ independently represents loweralkyl of $C_1-C_4$ or halo selected from the group consisting of bromo, chloro, fluoro, and iodo, subject to the limitation that at least one $R^2$ represents loweralkyl as defined. The compound wherein $R°$ represents hydrogen is named as 7-amino-3-carbamoyloxymethyl-3-cephem-4-carboxylic acid.

The compounds are obtained by cleavage of the "α-aminoadipoyl" group (5-amino-5-carboxyvaleryl) from 7-(5-amino-5-carboxyvaleramido)-3-carbamoyloxymethyl-3-cephem-4-carboxylic acid:

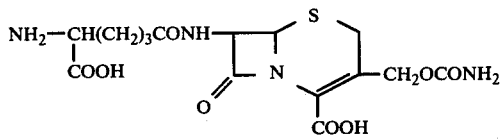

This compound is obtained by fermentation of *Streptomyces clavuligerus* NRRL 3585, and is alternately identified as antibiotic "A16886II". Suitable methods of cleaving the α-aminoadipoyl group include mild acid hydrolysis; treatment with nitrosyl chloride; treatment with phosphorus pentachloride or other acid halide; and intramolecular aminolysis. Of these methods, treatment with an acid halide is the preferred method.

In the acid halide and intramolecular aminolysis methods, the acid groups must be protected. Additionally, in the acid halide method, the amino group must be protected. Hence, the cleavage reactions actually involve compounds other than the 7-(5-amino-5-carboxyvaleramido)-3-carbamoyloxymethyl-3-cephem-4-carboxylic acid. Certain of these compounds of the formula

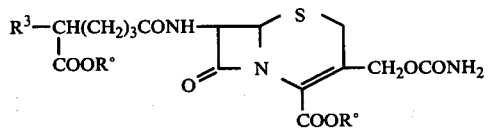

are preferred for the carrying out of these methods. In the above and like succeeding formulae, $R^3$ represents amino or acylamido as hereinbelow defined and $R°$ is as above defined, subject to the limitation that at least one of the following exists: (1) $R°$ represents $R^1$; or (2) $R^3$ represents acylamido as defined. These compounds are also claimed herein.

The 7-amino-3-carbamoyloxymethyl-3-cephem-4-carboxylic acid product can be reacylated to obtain novel derivatives, many of which exhibit enhanced antibacterial activity. The acylation can also be carried out with the corresponding ester, but resulting compounds must then be hydrolyzed since activity resides in only the free acid compounds.

DETAILED DESCRIPTION OF THE INVENTION

The compounds central to the present invention

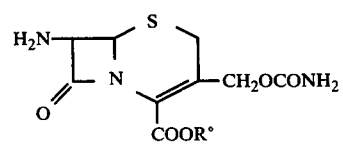

are prepared by cleavage of the α-aminoadipoyl group from 7-(5-amino-5-carboxyvaleramido)-3-carbamoyloxymethyl-3-cephem-4-carboxylic acid:

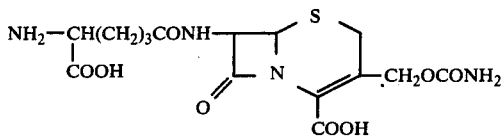

which compound is obtained by fermentation of an organism identified as *Streptomyces clavuligerus* NRRL 3585; the compound is alternately identified as antibiotic "A16886II." The organism which produces the compound has been placed on permanent deposit without restriction as to availability with the culture collection of the Northern Utilization Research and Development Division, Agricultural Research Service, U.S. Department of Agriculture (formerly Northern Regional Research Laboratories), Peoria, Illinois 61604, and is available to the public under culture No. NRRL 3585. The production of A16886II from *Streptomyces clavuligerus* NRRL 3585 is more fully described in Belgian Pat. No. 754,693.

The cleavage can be carried out in any of a number of reaction methods known for the cleavage of cephalosporin C to 7-aminocephalosporanic acid ("7-ACA"); mild acid hydrolysis; treatment with nitrosyl chloride; treatment with phosphorus pentachloride or other acid halide; or intramolecular aminolysis.

PHOSPHORUS PENTACHLORIDE OR OTHER ACID HALIDE TREATMENT

The preferred cleavage method is that involving treatment by phosphorus pentachloride or other acid halide. In this method, an agent capable of forming an imino halide, typically phosphorus pentachloride, is reacted with 7-(5-amino-5-carboxyvaleramido)-3-carbamoyloxymethyl-3-cephem-4-carboxylic acid of which the amino group and both carboxyl groups have been blocked:

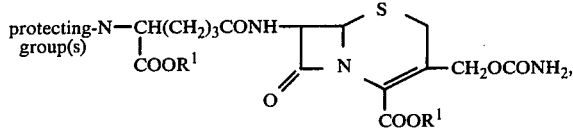

and the resulting imino halide (X being, for example, bromo or chloro):

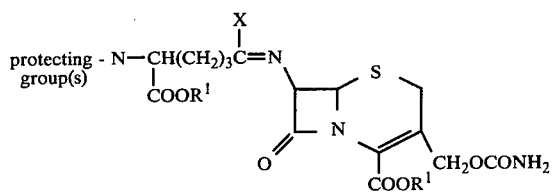

is further converted by reaction with an alcohol ($R^4OH$) into the imino ether:

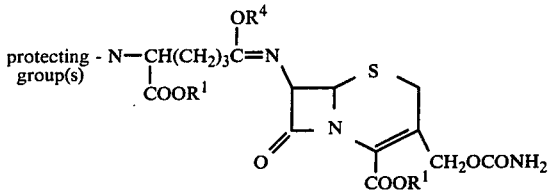

This imino ether is then hydrolyzed to obtain the desired 7-amino-3-carbamoyloxymethyl-3-cephem-4-carboxylic acid.

The reactions generally are conducted in accordance with those procedures employed for similar conversion of cephalosporin C to 7-ACA (see, e.g., British Pat. No. 1,041,985, issued September 7, 1966, to Ciba Limited). Thus, the 7-(5-amino-5-carboxyvaleramido)-3-carbamoyloxymethyl-3-cephem-4-carboxylic acid is first treated (1) to protect the amino group; and (2) to protect the carboxyl groups.

The protection of the amino group is conveniently obtained by reacting 7-(5-amino-5-carboxyvaleramido)-3-carbamoyloxymethylmethyl-3-cephem-4-carboxylic acid with a suitable acyl halide, anhydride, or ketene. The identity of the acylamido group thereby obtained is not critical. Generally suitable are acyl groups such as the following:

alkanoyl of $C_1$–$C_4$,
aroyl of $C_7$–$C_{11}$,
alkoxycarbonyl of $C_2$–$C_5$,
benzyloxycarbonyl,
cycloalkoxycarbonyl of $C_6$–$C_7$,
aryloxycarbonyl of $C_7$–$C_{11}$,
one of the above groups substituted with from one to three groups, each selected from the group consisting of halo, nitro, loweralkoxy of $C_1$–$C_4$, cyano, and, in the instance of aroyl and aryloxy, loweralkyl of $C_1$–$C_4$, and phthaloyl.

Halo is employed to refer to bromo, chloro, iodo and fluoro. Representative suitable groups include the following: formyl, acetyl, propionyl, chloroacetyl, dichloroacetyl, benzoyl, p-nitrobenzoyl, phthaloyl, p-methylbenzoyl, tert-butoxycarbonyl, phenoxycarbonyl, benzyloxycarbonyl, and the like.

The carboxyl groups of the 7-(5-amino-5-carboxyvaleramido)-3-carbamoyloxymethyl-3-cephem-4-carboxylic acid are protected by esterification. The identity of the ester group is not critical; suitable groups are those which can easily be split off after the protection is no longer required. Representative and suitable groups, when the esterification is carried out as a separate step include:

alkyl of $C_1$–$C_6$ such as methyl and tert-butyl,
2,2,2-trichloroethyl,
2-iodoethyl,
tert-alkenyl of $C_5$–$C_7$,
tert-alkynyl of $C_5$–$C_7$,
benzyl,
nitrobenzyl,
tetrahydropyranyl,
succinimidomethyl,
phthalimidomethyl,
methoxybenzyl,
dimethoxybenzyl,
cyanomethyl,
nitrophenyl,
dinitrophenyl, 2,4,6-trinitrophenyl,
bis(p-methoxyphenyl)methyl,
triphenylmethyl,
diphenylmethyl,
benzyloxymethyl,
loweralkanoyloxymethyl of $C_3$–$C_6$, such as pivaloyloxymethyl, and phenacyl.

While the protection of the carboxyl groups can be carried out at a separate step, it is often conveniently carried out as an initial part of the cleavage reactions, by employing either a reactant which will form a mixed anhydride, or a silane compound. The mixed anhydride is prepared in conventional procedures as, for example, by reacting the 7-(5-protected amino-5-carboxyvaleramido)-3-carbamoyloxymethyl-3-cephem-4-carboxylic acid with an acyl halide. The identity of the latter reactant, and its corresponding moiety in the mixed anhydride, is not critical. Suitable groups include the loweralkanoyl moieties and such moieties bearing substituents. However, owing to their ease of preparation, the simple loweralkanoyl groups, such as those containing from 2 to 4 carbon atoms, are preferred.

The silane compound to be used in protection of the carboxyl groups is suitably a compound of the formula

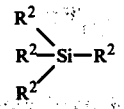

wherein each $R^2$ independently represents loweralkyl of $C_1$–$C_4$ or halo selected from the group consisting of bromo, chloro, fluoro, and iodo—subject to the limitation that at least one $R^2$ represents halo and at least one $R^2$ represents loweralkyl as defined. A preferred silane compound is trimethylchlorosilane. Other suitable compounds include dimethyldichlorosilane, methyltrichlorosilane, diethyldifluorosilane, bromotrimethylsilane, and the like. Such reagents protect the carboxyl groups but are readily removed by the hydrolysis of cleavage, without need of a separate removal step. The

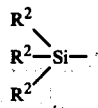

protecting group can also be introduced by reacting the 7-(5-amino-5-carboxyvaleramido)-3-carbamoyloxymethyl-3-cephem-4-carboxylic acid with a silylamide, urea, urethane, or like compound, as described in Belgian Pat. No. 737,761.

Alternately, the carboxyl and amino groups in the α-aminoadipoly side chain can be blocked by ring formation as, for example, by formation of an imidazolidine ring.

In conducting the initial reaction, the 7-(5-amino-5-carboxyvaleramido)-3-carbamoyloxymethyl-3-cephem-4-carboxylic acid, with the amino and carboxyl groups protected, is reacted with an agent capable of forming an imino halide. While phosphorus pentachloride is the preferred agent, other acid halides can be used. Thus, other suitable agents include phosphorus oxychloride, phosphorus trichloride, thionyl chloride, phosgene, oxalyl chloride, and the complex compound formed from o-dihydroxybenzene and phosphorus trichloride.

The starting compound and the imino-halide-forming agent are reacted with one another in any convenient fashion. Generally, the reaction consumes the reactants in amounts representing one molecular proportion of the starting compound and two molecular proportions of the imino-halide-forming agent. The reaction goes forward under temperatures of from −50° C. to 0° C., but is preferably conducted at temperatures of from −25° C. to −10° C. The reaction is preferably conducted in the presence of a tertiary amine, for example, triethylamine, pyridine, or dimethylaniline.

The resulting imino halide is reacted with an alcohol $R^4$-OH) in the presence of a tertiary amine to form an imino ether. Suitable alcohols include loweralkanols, such as methanol, ethanol, n-propyl alcohol, benzyl alcohol and the like. The reaction is conducted in accordance with standard procedures, and the resulting imino ether is then hydrolyzed to the desired 7-amino compound. The hydrolysis is carried out in known manner with water, preferably with a mineral acid or an organic acid. Suitable acids include hydrochloric acid, sulfuric acid, phosphoric acid, fluorboric acid, formic acid, trifluoroacetic acid, or p-toluenesulfonic acid.

This hydrolysis serves also to remove any acid-protecting group vulnerable to aqueous conditions; and, depending on the amount or identity of acid utilized, hydrolysis of other acid-protecting groups may also occur. In the instance where the acid-protecting group is not removed by the hydrolysis conditions used previously, the ester group can be removed in a separate step. Such removal is carried out under conditions which will not effect the remainder of the molecule, typically hydrogenolysis or acid hydrolysis. In all cases, the use of trifluoroacetic acid and anisole is acceptable and preferred, and, in the case of those ester groups comprising an aryl group, the use of catalytically activated hydrogen is also a preferred method.

NITROSYL CHLORIDE TREATMENT

In addition to the foregoing method of cleavage, the 7-(5-amino-5-carboxyvaleramido)-3-carbamoyloxymethyl-3-cephem-4-carboxylic acid can be cleaved by treatment with nitrosyl chloride. The reaction is generally conducted in accordance with those procedures reported for the conversion of cephalosporin C to 7-ACA by treatment with nitrosyl chloride (J.A.C.S., Vol. 91:6; March 12, 1969, page 1396 et seq.). Thus, the reaction is preferably conducted in formic acid as solvent, although acetic acid can also be used. Other solvents possess limited solubility for the starting 7-(5-amino-5-carboxyvaleramido)-3-carbamoyloxymethyl-3-cephem-4-carboxylic acid, and yields employing such solvents are generally lower. The product of the reaction is 7-amino-3-carbamoyloxymethyl-3-cephem-4-carboxylic acid. Yields are dependent on reaction temperature and reaction time. Optimum results are obtained when the reaction temperature does not exceed 30° C. and the reaction period is short.

Acid Hydrolysis

In addition, 7-(5-amino-5-carboxyvaleramido)-3-carbamoyloxymethyl-3-cephem-4-carboxylic acid can be cleaved by mild acid hydrolysis likewise to yield 7-amino-3-carbamoyloxymethyl-3-cephem-4-carboxylic acid. The reaction generally is conducted in accordance with those procedures reported for the cleavage, by mild acid hydrolysis, of cephalosporin C to obtain 7-ACA ;(Biochem. J., Vol. 79, page 408 et seq. (1961)).

Intramolecular Aminolysis

Finally, the starting 7-(5-amino-5-carboxyvaleramido)-3-carbamoyloxymethyl-3-cephem-4-carboxylic acid can also be cleaved by the intramolecular aminolysis method reported in Helv. Chim. Acta, 51, 1008 (1968) for conversion of cephalosporin C to 7-ACA. In this cleavage method, the 7-(5-amino-5-carboxyvaleramido)-3-carbamoyloxymethyl-3-cephem-4-carboxylic acid with both carboxyl groups protected is treated with pyridine and acetic acid in methylene chloride, preferably at room temperature. The protection of the carboxylic groups is accomplished as discussed above regarding the acid halide cleavage method, except that the silyl groups and the mixed anhydride protecting groups are not suitable. The reaction yields the corresponding 7-amino-3-carbamoyloxymethyl-3-cephem-4-carboxylic acid ester, which can be hydrolyzed to the free acid.

Derivatives

By the various cleavage methods described hereinabove, there are obtained compounds of the formula

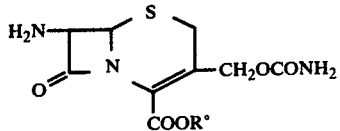

From these compounds are prepared derivative compounds of the formula

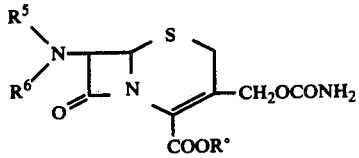

Those of the derivatives wherein $R^\circ$ = hydrogen exhibit antibacterial activity, and those wherein $R^\circ = R^1$ (esters) are useful as intermediates. The preparation of all of the derivatives is by acylation of the corresponding 7-amino compound. Inasmuch as the antibacterial activity is exhibited by compounds having a free acid at the 4-position, hydrolysis must be carried out either prior to or following acylation, in the case of starting materials wherein $R^\circ = R^1$ (esters). The pharmaceutically acceptable cationic salts and acid addition salts of certain of the derivatives are prepared in conventional procedures.

In the derivatives

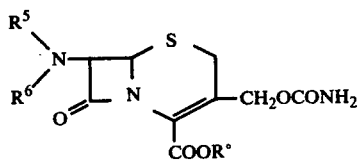

the identity of $R^5$ and $R^6$ is not critical, since many derivatives can be made from the nucleus and all exhibit antibacterial activity. Representative compounds are those wherein, both $R^5$ and $R^6$ being taken separately, $R^5$ represents hydrogen and $R^6$ represents
  $C_1$-$C_8$ alkanoyl;
  azidoacetyl;
  cyanoacetyl;
  haloacetyl;

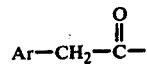

where Ar denotes phenyl, thienyl, furyl, pyrrolyl, or phenyl substituted with from one to three substituents selected from the group consisting of fluorine, chlorine, bromine, iodine, trifluoromethyl, hydroxy, $C_1$-$C_3$ alkyl, $C_1$-$C_3$ alkoxy, cyano, and nitro;

where Ar' represents phenyl, pyridyl, or substituted phenyl as defined above, and Y is oxygen or sulfur;

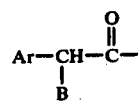

where Ar is as defined above, and B is -$NH_2$, an amino group protected with benzyloxycarbonyl, $C_1$-$C_4$ alkoxycarbonyl, cycloalkoxycarbonyl, triphenylmethyl, 2,2,2-trichloroethoxycarbonyl, the group of the formula

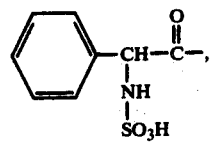

the group of the formula

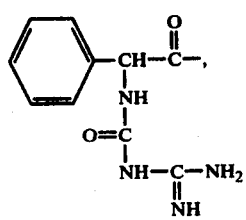

the enamine from methyl acetoacetate, or the like, or B is —OH, —COOH, or such groups protected by esterification, or B is —CN or —$N_3$;

2-(3-sydnone)alkanoyl of $C_2$-$C_3$; or 2-(1H-tetrazol-1-yl)acetyl.

Other representative compounds are those wherein both $R^5$ and $R^6$ are taken together with the nitrogen to which they are bonded and denote a cyclic imide group from a $C_3$-$C_{12}$-hydrocarbon dicarboxylic acid.

All of these derivatives are useful as intermediates in the preparation of other derivatives. Preferred compounds for purposes of antibacterial activity are those wherein $R^5$ represents hydrogen and $R^6$ represents cyanoacetyl;

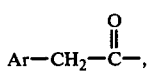

as defined;

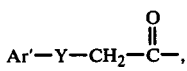

as defined

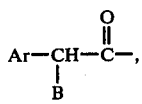

wherein Ar is as defined and B is -NH$_2$, the group of the formula

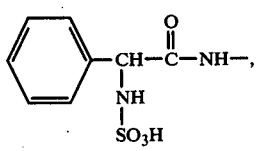

the group of the formula

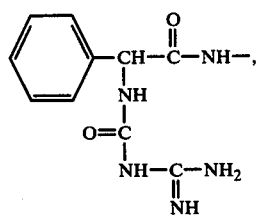

—OH, —COOH, —CN, or —N$_3$; 2-(3-sydnone)alkanoyl of C$_2$-C$_3$; or 2-(1H-tetrazol-1-yl)acetyl.

Representative $R^6$ groups include the following:
formyl,
acetyl,
bromoacetyl,
chloracetyl,
azidoacetyl,
cyanoacetyl,
2-thienylacetyl,
2-furylacetyl,
2-pyrrolylacetyl,
phenylacetyl, (p-hydroxyphenyl)acetyl,
phenoxyacetyl, (2-pyridylthio)acetyl,
(phenylthio)acetyl,
(2,5-dichlorophenylthio)acetyl,
(3,4-dichlorophenylthio)acetyl,
(3,5-dichlorophenylthio)acetyl,
(p-nitrophenyl)acetyl
2-amino-2-phenylacetyl,
2-amino-2-(m-hydroxyphenyl)acetyl,
2-hydroxy-2-phenylacetyl,
2-hydroxy-2-(m-hydroxyphenyl)acetyl,
2-carboxy-2-phenylacetyl,
3-sydnoneacetyl, and
(1H-tetrazol-1-yl)acetyl.

In the instance of compounds where $R^6$ represents

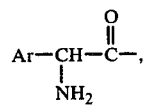

the compounds may actually exist in the form of an internal salt of the amino group with the carboxyl group. However, pharmaceutically acceptable acid addition salts of such compounds can be prepared and are within the scope of the present invention. Likewise, in the instance of all derivatives, cationic salts can be prepared and are within the scope of the present invention. All salts exhibit the antibacterial activity of the corresponding free acids or free bases.

In preparing acid addition salts, the free amine is reacted with an inorganic or organic acid. Representative suitable acids include hydrochloric acid, hydrobromic acid, hydriodic acid, sulfuric acid, phosphoric acid, acetic acid, benzoic acid, sulfamic acid, tartaric acid, citric acid, maleic acid, succinic acid, ascorbic acid, and glycolic acid.

The cationic salts are prepared by reacting the free acid with inorganic and organic bases and salts. Exemplary of these salts are ammonium and substituted ammonium salts; alkali metal salts, such as sodium, potassium, lithium, cesium, and rubidium; and alkaline earth metal salts such as calcium, strontium, and barium; copper, zinc, magnesium, and silver. In the instance of organic bases, the identity of the base is not critical, although, in general, a base having a pKa of, numerically, 3.0 or above in water is preferred. Representative suitable organic bases include benzylamine, methylamine, diethylamine, triethylamine, procaine, diisopropylamine, ethanolamine, cyclohexylamine, dicyclohexylamine, diphenylamine, di-n-butylamine, quinoline, and pyridylamine.

Pharmaceutically acceptable salts are generally preferred for pharmaceutical applications. However, all salts are useful as intermediates in production, separation, and purification. For therapeutic purposes, pharmaceutically acceptable salts are generally equivalent to the free base or acid; however, particular salts are occasionally preferred due to a favorable property, such as solubility, conferred by the salt-forming moiety.

Bioautographic Confirmation

Confirmation of identity, as is conventional, can be established by bioautographic evaluation. In data reported hereinbelow, bioautographic analysis was conducted in either or both of two ways: acylation prior to developement of the chromatogram and acylation after development of the chromatogram.

In the former procedure, an amount of the sample was applied at the point of application and allowed to dry. This was followed by the application, at the same point, of an aqueous solution containing 2 percent sodium bicarbonate. The volume used depended upon the amount of the sample applied. The sodium bicarbonate solution was immediately followed with an amount of a 0.3 percent solution of a selected acyl halide in petroleum ether, applied to the same point. The chromatogram was then handled in the normal manner for bioautographic detection of the compound, in this instance, of the acylated derivative.

In the instance of acylation after development of the chromatogram, sample application and chromatographic development were done in the normal manner. The developed chromatogram was then sprayed, first with an aqueous solution containing 2 percent sodium bicarbonate, followed with 0.3 percent solution of a selected acyl halide in petroleum ether. The chromatogram was then handled in the normal manner for bioautographic detection of the compound. Acylation prior to development of the chromatogram allows the compound to migrate as the acylated material, whereas acylation after development allows the compound to migrate as the nucleus.

In some of the bioautographic data reported herein, "$R_{CV}$" values were obtained. The $R_{CV}$ value is the ratio of movement expressed relative to that of cephalosporin V (7-(phenoxyacetamido)cephalosporanic acid) which was given a value of 1.0.

The following examples illustrate the present invention and will enable those skilled in the art to practice the same.

EXAMPLE 1:

Preparation of 7-(5-(Chloroacetamido)-5-Carboxyvaleramido)-3-Carbamoyloxymethyl-3-Cephem-4-Carboxylic Acid Five hundred milligrams of 7-(5-amino-5-carboxyvaleramido)-3-carbamoyloxymethyl-3-cephem-4-carboxylic acid was dissolved in 10 milliliters of sodium borate buffer and 650 milligrams of chloroacetyl chloride was added at ~20° C., keeping the pH of 9.0-9.5 by addition of 40 percent sodium hydroxide solution. After addition of the chloroacetyl chloride was complete, the reaction mixture was stirred for thirty minutes. The pH was adjusted to about 6.5 by addition of 30 percent sulfuric acid; then 10 milliliters of ethyl acetate:ethanol (9:1) was added, and the pH adjusted to 2.0. The organic layer was separated, dried over anhydrous magnesium sulfate, and ether was added, resulting in the precipitation of the desired 7-(5-(chloroacetamido)-5-carboxyvaleramido)-3-carbamoyloxymethyl-3-cephem-4-carboxylic acid. It was separated as a white powder, 195 milligrams, and characterized: titration (in 66 percent dimethylformamide): initial pH 3.9 pKa's at 4.8 and 6.1. Amino acid analysis: 0.12 $\mu$M./mg. of glycine and 1.9 $\mu$M./mg. of $\alpha$-aminoadipic acid. NMR in dimethylsulfoxide-$d_6$ showed bands at 6.36, 6.58 (2-CH$_2$, q, J = 18); 5.08, 5.35 (3-CH$_2$, q, J = 13); 4.89 (H-6, d, J= 5.0); 4.34 (H-7, q, J = 5.0, 8.0); 3.41 (CONH$_2$, s); 5.87 (COCH$_2$Cl, s); 1.17 $\tau$ (7-NH, d, J = 8.0 Hz).

In all the NMR data herein, the chemical shifts are expressed in $\tau$ values, with tetramethylsilane as internal standard. Coupling constants are expressed in Hz. s = singlet, d = doublet, q = quartet, m = multiplet.

EXAMPLE 2

Preparation of 7-(5-(Chloroacetamido)-5-Carboxyvaleramido)-3-Carbamoyloxymethyl-3-Cephem-4-Carboxylic Acid, Dimethyl Ester 7-(5-(Chloroacetamido)-5-carboxyvaleramido)-3-carbamoyloxymethyl-3-cephem-4-carboxylic acid was prepared as reported in the preceding example, using 1.0 gram of 7-(5-amino-5-carboxyvaleramido)-3-carbomoyloxymethyl-3-cephem-4-carboxylic acid and 1.3 grams of chloroacetyl chloride, except that the compound was not separated from the reaction mixture. Instead, there was added to the reaction mixture, after drying over magnesium sulfate, excess diazomethane. The solution was then evaporated to about 10 milliliters and filtered to separate the desired dimethyl ester product, 620 milligrams, m.p., 224°-228° C. A 100-milligram portion was recrystallized, 231°-232° C.

Calc., for $C_{19}H_{25}O_9N_4SCl$: C, 43.80; H, 4.84; N, 10.78; S, 6.16; Cl, 6.81; OCH$_3$, 11.91. Found: C, 43.93; H, 4.88; N, 10.52; S, 6.12; Cl, 7.05; OCH$_3$, 11.78.

Further analysis was conducted. UV (ethanol): $\alpha$ max 261 nm. ($\epsilon$ = 7900). IR (nujol): 1755 ($\beta$-lactam), 1725 (ester), 1700, 1610 (carbamate), 1670, 1640 cm$^{-1}$(amide). Amino acid analysis: 0.19 $\mu$M./mg. of glycine and 1.6 $\mu$M./mg. of $\alpha$-aminoadipic acid. NMR in dimethylsulfoxide-$d_6$ showed bands at 6.33, 6.54 (2-CH$_2$, q, J = 18); 6.34, 6.20 (COOCH$_3$, s); 5.11, 5.39 (3-CH$_2$, q, J = 13); 4.31 (H-7, q, J = 5.0, 8.0); 4.85 (H-6, d, J = 5.0); 3.41 (CONH$_2$, s); 5.87 (COCH$_2$Cl, s); 1.15 $\tau$ (7-NH, d, J = 8.0 Hz).

EXAMPLE 3

Preparation of 7-(5-Phthalimido-5-Carboxyvaleramido-3-Carbamoyloxymethyl-3-Cephem-4-Carboxylic Acid To a stirred solution of 15 grams of 7-(5-amino-5-carboxyvaleramido)-3-carbamoyloxymethyl-3-cephem-4-carboxylic acid in 150 milliliters of 10 percent potassium hydrogen phosphate buffer solution (adjusted to pH 9.1 by addition of 25 percent potassium phosphate solution) was added 9.9 grams of N-carbethoxy phthalimide in 75 milliliters of acetone. The reaction mixture was stirred at room temperature for one hour at pH 9.1, diluted with water to 300 milliliters, and the pH adjusted to 7.0 by addition of phosphoric acid. The acetone was then evaporated and the reaction mixture extracted with ethyl acetate:ethanol (88:12) to remove the phthalimide. The pH of the aqueous layers was adjusted to 2 by addition of phosphoric acid and the mixture extracted with ethyl acetate:ethanol (88:12). The extract was dried with anhydrous magnesium sulfate and filtered, and the filtrate evaporated to dryness, leaving as a residue the desired 7-(5-phthalimido-5-carboxyvaleramido)-3-carbamoyloxymethyl-3-cephem-4-carboxylic acid as a foam. It was digested three times with 500-milliliter aliquots of ether. The ether washed product amounted to 17.05 grams.

Physical data was obtained on the ether washed product. Titration in 66 percent dimethylformamide at an initial pH of 4.2 showed pK'$_{a1}$ = 5.5 and pK'$_{a2}$ = 6.7. Infrared analysis showed the $\beta$-lactam at 1765 cm.$^{-1}$; UV showed a peak a $\lambda$ max. 265 nm ($\epsilon$ 4300). NMR in dimethylsulfoxide-$d_6$ showed bands at 6.66; 6.40 (2-CH$_2$, q, J = 18); 5.36, 5.06 (3-CH$_2$, q, J = 13); 4.91 (H-6, d, J = 4.5); 4.36 (H-7, q, J = 4.5, 8.0); 3.38 (CONH$_2$, s); 2.05 (C$_6$H$_4$, s); 1.18 $\tau$ (7-NH, d, J = 8.0 Hz).

EXAMPLE 4

Preparation of 7-(5-Phthalimido-5-carboxylvaleramido)3-Carbamoyloxymethyl-3-Cephem-4-Carboxylic Acid, Dimethyl Ester One gram of 7-(5-phthalimido-5-carboxyvaleramido)-3-carbamoyloxymethyl-3-cephem-4-carboxylic acid was dissolved in 10 milliliters of ethanol and excess diazomethane was added. The corresponding dimethyl ether crystallized out, the ether and excess diazomethane were evaporated, and the ester filtered, 400 milligrams, m.p., 151°-156° C. Two hundred milligrams of this product were recrystallized from methylene chloride:ethanol, yielding 150 milligrams of crystals, m.p., 153°–155° C.

Physical data was obtained on this product. IR showed the β-lactam band at 1780 cm.$^{-1}$; and UV showed a band at λ max. 261 nm (ε 8000). NMR analysis in dimethylsulfoxide-$d_6$ showed bands at 6.63, 6.38 (2-$CH_2$, q, J = 18); 6.33, 6.21 ($COOCH_3$, s); 5.40, 5.11 (3-$CH_2$, q, J = 13); 4.34 (H-7, q, J = 4.5, 8.5); 4.88 (H-6, d, J = 4.5); 3.38 ($CONH_2$, s); 2.05 ($C_6H_4$, s); 1.17 τ (7-NH, d, J = 8.5 Hz). Mass spectrum: m/e = 231.048 (calc. for $C_8H_{11}O_4N_2S$ = 231.044, dihydrothiazine fragment); m/e = 345.106 (calc. for $C_{17}H_{17}O_6N_2$ = 345.109, side-chain fragment).

EXAMPLE 5

Preparation of 7-Amino-3-Carbamoyloxymethyl-3-Cephem-4-Carboxylic Acid by Phosphorus Pentachloride Cleavage of 7-(5-Phthalimido-5-Carboxyvaleramido)-3-Carbamoyloxymethyl-3-Cephem-4-Carboxylic Acid To a stirred slurry of 3.0 grams of 7-(5-phthalimido-5-carboxyvaleramido)-3-carbamoyloxymethyl-3-cephem-4-carboxylic acid in 50 milliliters of absolute methylene chloride were added 2.9 milliliters of absolute pyridine and 4.5 milliliters of trimethylchlorosilane, to protect both of the carboxyl groups. The resulting reaction mixture was stirred for two and one-half hours, then cooled to −12° C. in a carbon tetrachloride: dry ice bath. To this were added 5.6 milliliters of absolute pyridine in one lot, and then 36.2 milliliters of a 10 percent solution of phosphorus pentachloride in absolute methylene chloride, dropwise, maintaining the temperature at −12° C. The reaction mixture was stirred for two and one-half hours, 40 milliliters of absolute methanol was added dropwise at −12° C. and stirred for thirty minutes, and for another thirty minutes at room temperature. Then 10 milliliters of 50 percent formic acid was added dropwise, the pH adjusted to 2 by addition of triethylamine, and the reaction mixture stirred for forty-five minutes. The solution became cloudy. Then the pH was adjusted to 3.4, and the reaction mixture was refrigerated overnight and filtered, yielding 600 milligrams of 7-amino-3-carbamoyloxymethyl-3-cephem-4-carboxylic acid, 40 percent yield. This was taken up in 5 milliliters of water, stirred and filtered. The solid was washed with about 2 milliliters of water and 10 milliliters of acetone, yielding 450 milligrams of purified 7-amino-3-carbamoyloxymethyl-3-cephem-4-carboxylic acid, 30 percent yield.

Calc., for $C_9H_{11}N_3O_5S$: C, 39.56; H, 4.06; N, 15.38; S, 11.73. Found: C, 39.70; H, 4.12; N, 15.34; S, 11.98.

Physical data was obtained on a sample prepared in the foregoing procedures: UV (in sodium bicarbonate buffer, pH 8.1); λ max. 262 nm (ε 6600). IR (mull): 1800 (β-lactam), 1700 cm$^{-1}$ (carbamate). NMR (deuterium oxide: sodium bicarbonate): 4.53 (H-7, J = 4.5); 4.91 (H-6, J = 4.5); 5.09, 5.32 (3-$CH_2$, J = 13); 6.31, 6.62 τ (2-$CH_2$, J = 18.5 Hz).

In addition, a bioautogram was conducted on a sample of 7-amino-3-carbamoyloxymethyl-3-cephem-4-carboxylic acid prepared in the foregoing procedures. The bioautogram was conducted with a solvent system of n-propanol:water (7:3); the sample was acylated with phenylacetyl chloride, then developed with B. subtilis. The sample showed an $R_f$ value of 0.26.

EXAMPLE 6

Preparation of 7-Amino-3-Carbamoyloxymethyl-3-Cephem-4-Carboxylic Acid by Phosphorus Pentachloride Cleavage of 7-(5-Chloroacetamido-5-Carboxyvaleramido)-3-Carbamoyloxymethyl-3-Cephem-4-Carboxylic Acid To a stirred slurry of 100 milligrams of 7-(5-(chloroacetamido)-5-carboxyvaleramido)-3-carbamoyloxymethyl-3-cephem-4-carboxylic acid in 10 milliliters of absolute methylene chloride was added 0.1 milliliters of pyridine and 0.15 milliliters of trimethylchlorosilane. The reaction mixture was stirred for two and one-half hours at room temperature. Then the reaction mixture was cooled to −15° C. and 0.2 milliliter of pyridine (in one lot), and 1.2 milliliter of 10 percent phosphorus pentachloride in absolute methylene chloride added dropwise, and the mixture stirred at −15° C. for two and one-half hours. Then 2 milliliters of absolute methanol were added, and the reaction mixture stirred for thirty minutes at −15° C. and for another thirty minutes at room temperature. Then 0.3 milliliter of 50 percent formic acid was added and the pH adjusted to 2 by adding triethylamine and stirring for forty-five minutes. The reaction mixture became cloudy. Then the pH was adjusted to 3.4, and the reaction mixture stirred for two hours in an ice bath and filtered. There was obtained 15 milligrams of 7-amino-3-carbamoyloxymethyl-3-cephem-4-carboxylic acid. It was identified by bioautogram and UV, which showed λ max. 262 nm (ε 5800).

EXAMPLE 7

Preparation of 7-Amino-3-Carbamoyloxymethyl-3-Cephem-4-Carboxylic Acid by Nitrosyl Chloride Cleavage 7-(5-carboxyvaleramido)-3-carbamoyloxymethyl-3-cephem-4-carboxylic acid (750 milligrams) was dissolved in 10 milliliters of formic acid at 0° C. To this solution was added 0.210 gram of nitrosyl chloride in 1 milliliter of formic acid; the resulting solution was stirred for thirty minutes, and 5 milliliters of ethanol were added and the reaction mixture stirred another five minutes. The solvents were then evaporated to dryness in vacuum to separate the desired 7-amino-3-carbamoyloxymethyl-3-cephem-4-carboxylic acid. A portion was subjected to bioautographic analysis. This analysis confirmed the presence of 7-amino-3-carbamoyloxymethyl-3-cephem-4-carboxylic acid by reference to bioautographic analysis of a sample of the same compound prepared as reported in Example 5 (phosphorus pentachloride cleavage). The product was later purified by column chromatography.

EXAMPLE 8

Preparation of 7-(2-(2-Thienyl)acetamido)-3-Carbamoyloxymethyl-3-Cephem-4-Carboxylic Acid To a solution of 100 milligrams (0.6 millimole) of 2-thiopheneacetyl chloride in 5 milliliters of absolute methylene chloride was added slowly a slurry of 137 milligrams (0.5 millimole) of 7-amino-3-carbamoyloxymethyl-3-cephem-4-carboxylic acid and 86 milligrams (0.9 millimole) of triethylamine in 10 milliliters of absolute methylene chloride. The addition was carried out at −15° C., with stirring. After the addition, stirring was continued for two hours at −15° C. and for one and one-half hours at room temperature. The reaction mixture was then cooled and filtered to separate the precipitated solid. The solid, 80 milligrams, was analyzed on bioautogram. Bioautogram showed that approximately 50 percent of the sample was 7-amino-3-carbamoyloxymethyl-3-cephem-4-carboxylic acid and another 50 percent was the desired 7-(2-(2-thienyl)acetamido)-3-carbamoyloxymethyl-3-cephem-4-carboxylic acid.

EXAMPLE 9
Preparation of 7-(2-(2-Thienyl)acetamido)-3-Carbamoyloxymethyl-3-Cephem-4-Carboxylic Acid The same reaction as in the preceding example was reported but scaled up to 273 milligrams of 7-amino-3-carbamoyloxymethyl-3-cephem-4-carboxylic acid (1.0 millimole) and reacted at −15° C. for two hours and at room temperature for another three hours. Enough saturated sodium bicarbonate was added, with stirring, to bring the pH to 8.1. The reaction mixture was extracted, and then the aqueous layer was acidified to about 2, extracted with 100 milliliters of ethyl acetate:ethanol (80:12), dried with anhydrous magnesium sulfate, and evaporated to dryness, yielding 250 milligrams. The sample thus obtained was washed twice with 50 milliliter-portions of ether to remove any thiopheneacetic acid. The residue, 100 milligrams, was dissolved in acetone, then ethyl acetate added and the acetone evaporated. The desired 7-(2-(2-thienyl)acetamido)-3-carbamoyloxymethyl-3-cephem-4-carboxylic acid precipitated and was separated by filtration.

The separated product was dissolved in two milliliters of hot acetone, and then five milliliters of ethyl acetate was added. The resulting solution was boiled down to about one milliliter, when the product precipitated out. This was repeated twice and the purified product obtained as a powder, m.p., 145°–150° C.

Calc. for $C_{15}H_{15}O_6N_3S_2$: C, 45.33; H, 3.80; N, 10.57; S, 16.14. Found: C, 45.32; H, 4.10; N, 10.31; S, 15.92.

Further analysis was carried out. IR (mull): 1760 cm.$^{-1}$ ($\beta$-lactam). UV (ethanol) $\lambda$ max. 258 ($\epsilon$ 7000) (3-cephem); 237 nm ($\epsilon$ 12,200) (thiophene). NMR (dimethylsulfoxide-$d_6$): 0.90 (7-NH, d, J = 8.5); 2.55–2.75 and 2.95–3.20 (three thiophene protons, m); 3.43 (CONH$_2$, s); 4.33 (H-7, q, J = 8.5, 4.5); 4.88 (H-6, d, J = 4.5); 5.07, 5.36 (3-CH$_2$, 2d, J = 13); 6.22 (CH$_2$ of thiophene acetyl, s); 6.37, 6.59 $\tau$ (2-CH$_2$, 2d, J = 18.5 Hz).

EXAMPLE 10
Preparation of 7-(2-(2-Thienyl)acetamido)-3-Carbamoyloxymethyl-3-Cephem-4-Carboxylic Acid, Methyl Ester 7-(2-(2-Thienyl)acetamido)-3-carbamoyloxymethyl-3-cephem-4-carboxylic acid (50 milligrams) in ethanol was reacted with excess diazomethane. After five minutes the excess diazomethane was evaporated and the desired methyl ester crystallized with ethanol, then with chloroform, and with acetone. Nine milligrams of the desired 7-(2-(2-thienyl)acetamido)-3-carbamoyloxymethyl-3-cephem-4-carboxylic acid, methyl ester were obtained, m.p., 212°–214° C.

Calc. for $C_{16}H_{17}N_3O_6S_2$: C, 46.71; H, 4.16; N, 10.21; S, 15.59. Found: C, 46.57; H, 4.12; N, 10.44; S, 15.30.

Further analysis was conducted. IR (mull) 1770 cm.$^{-1}$ ($\beta$-lactam). UV (ethanol) $\lambda$ max. 262 ($\epsilon$ 7200) (3-cephem); 237 nm ($\epsilon$ 12000) (thiophene) NMR (dimethylsulfoxide-$d_6$) 0.88 (NH, d, J = 8.2); 2.55–2.70 and 2.95–3.10 (three thiophene protons, m); 3.41 (CONH$_2$, s); 4.29 (H-7, q, J = 8.2, 4.5); 4.84 (H-6, d, J = 4.5); 5.1 and 5.4 (3-CH$_2$, 2d, J = 13); 6.21 (CH$_2$ of thiophene acetyl and COOCH$_3$, s); 6.34, 6.55 $\tau$ (2-CH$_2$, 2d, J = 18.5 Hz).

Mass spectrum: $M^+$ = 411.055 (calc. for $C_{16}H_{17}O_6N_3S_2$ = 411.056); m/e = 231.043 (calc. for $C_8H_{11}O_4N_2S$ = 231.044, dihydrothiazine fragment); m/e = 181.019 (calc. for $C_8H_7O_2NS$ = 181.020, sidechain fragment).

EXAMPLE 11
Preparation of -Phenoxyacetamido)-(2-Phenoxyacetamido)-3-Carbamoyloxymethyl-3-Cephem-4-Carboxylic Acid A portion of 7-amino-3-carbamoyloxymethyl-3-cephem-4-carboxylic acid, prepared in the same procedures as those described in Example 5, was dissolved in a dilute aqueous solution of sodium bicarbonate. About 1 $\mu$l of this solution was applied to Whatman's No. 1 paper previously buffered with 0.1 N sodium acetate, pH 4.6, and allowed to dry. Thereafter, about 1 $\mu$l of an aqueous solution containing 2 percent sodium bicarbonate was applied, followed immediately by about 1 $\mu$l of 0.3 percent phenoxyacetyl chloride in petroleum ether. Thereafter, the chromatogram was handled in conventional techniques for bioautographic detection of compounds; it was developed with methyl ethyl ketone:water (92:8). The organism employed for assay was B. subtilis. The 7-(2-phenoxyacetamido)-3-carbamoyloxymethyl-3-cephem-4-carboxylic acid thus prepared and evaluated exhibited an $R_{CV}$ value of 0.50.

EXAMPLE 12
Preparation of 7-(2-Phenylacetamido)-3-Carbamoyloxymethyl-3-Cephem-4-Carboxylic Acid Another 1 $\mu$l portion of the 7-amino-3-carbamoyloxymethyl-3-cephem-4-carboxylic acid-containing solution, prepared as reported in Example 11, was treated as described in Example 11 except that the acyl halide was phenylacetyl chloride, and the resulting product was 7(2-phenylacetamido)-3-carbamoyloxymethyl-3-cephem-4-carboxylic acid. It exhibited an $R_{CV}$ value of 0.42.

EXAMPLE 13
Preparation of 7-(2-(2-Thienyl)Acetamido-3-Carbamoyloxymethyl-3-Cephem-4-Carboxylic Acid A third 1 $\mu$l portion of the 7-amino-3-carbamoyloxymethyl-3-cephem-4-carboxylic acid-containing solution, prepared as reported in Example 11, was treated as described in Example 11, except that the acyl halide was 2-thiopheneacetyl chloride, and the resulting product was 7-(2-(2-thienyl)acetamido)-3-carbamoyloxymethyl-3-cephem-4-carboxylic acid. It exhibited an $R_{CV}$ value of 0.39.

EXAMPLES 14–20

Other representative examples of derivative compounds include the following:
  7-mandelamido-3-carbamoyloxymethyl-3-cephem-4-carboxylic acid
  7-(2-(2-pyridylthio)acetamido)-3-carbamoyloxymethyl-3-cephem4-carboxylic acid 7-(2-amino-2-phenylacetamido)-3-carbamoyloxymethyl-3-cephem-4-carboxylic acid 7-(2-(1H-tetrazol-1-yl)acetamido)-3-carbamoyloxymethyl-3-cephem4-carboxylic acid 7-(2-(3-sydnone)acetamido)-3-carbamoyloxymethyl-3-cephem-4-carboxylic acid 7-(2-(2-furyl)acetamido)-3-carbamoyloxymethyl-3-cephem-4-carboxylic acid 7-(2-(2-pyrrolyl)acetamido)-3-carbamoyloxymethyl-3-cephem-4-carboxylic acid

EXAMPLES 21-23

Various of the compounds of the present invention were evaluated for antibacterial activity by the "gradient plate" method of Bryson et al. ("Microbial Selection," *Science,* 116: 45–51 (1952)) modified by Godzeski et al. ("Cephalothin, a New Cephalosporin with a Broad Antibacterial Spectrum," *Appl. Microbiol.,* 11: 122–127 (1963)). The evaluation showed the following results:

TABLE 1

| Compound | Penicillin* resistant Staph. (V-41) | Penicillin* resistant Staph. (V-32) | Methicillin* resistant Staph. (X-400) | Penicillin* resistant Staph. (V-84) | N9 Shigella sp. | N10 Escherichia sp. | X26 Escherichia sp. | X68 Aerobacter aerogenes | X514 Salmonella heidelberg | X518 Pseudomonas aeruginosa | X99 Serratia marcescens |
|---|---|---|---|---|---|---|---|---|---|---|---|
| 7-(2-Thienyl)acetamido)-3-carbamoyloxymethyl-3-cephem-4-carboxylic acid | 0.2 1.0 0.2 0.7 1.5 1.0 | 0.5 1.0 0.2 0.6 1.1 1.5 | >20 9.6 5.7 4.2 >20 >20 | 0.4 0.8 0.1 0.1 1.0 1.7 | 30.0 >50 3.5 | 19.5 >50 4.7 | 1.0 — 0.7 | 3.5 65 1.0 | 2.6 >50 0.6 | >50 >50 >50 | >50 >50 >50 |
| 7-(Phenoxyacetamido)-3-carbamoyloxymethyl-3-cephem-4-carboxylic acid | | | | | | | | | | | |
| 7-Mandelamido-3-carbamoyloxymethyl-3-cephem-4-carboxylic acid | | | | | | | | | | | |

*In the case of the resistant organisms, evaluations were carried out with both the compound alone and in combination with 40 percent serum. The upper figure in each set is with the compound, alone, the lower, in combination with serum.

EXAMPLE 24

7-(2-(2-Thienyl)acetamido)-3-carbamoyloxymethyl-3-cephem-4-carboxylic acid was also evaluated in accordance with the broth dilution procedure of Wick ("Delineation of the Differences of Various Bacterial Susceptibility Tests with Cephalexin," Antimicrobial Agents and Chemotherapy, 1968, pages 435–441). The evaluation showed a minimum inhibitory concentration for the compound of 0.125 μg./ml. against *Streptococcus pyogenes* and 2.0 μg./ml. against *Staphylococcus aureus*. Also, the same compound was evaluated in vivo in accordance with the procedure described by Wick et al. ("Guide to Antibiotic Therapy of Experimental Bacterial Infections in Mice", *J. Bact.*, 81: 233–235 (1960)). The ED$_{50}$ thus determined was 1.2 mg./kg. against *S. pyogenes* and 2.0 mg./kg. against *S. aureus*.

I claim:

1. The compound of the formula

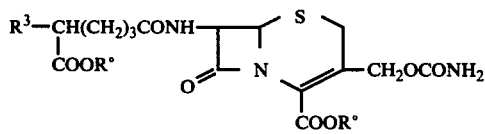

wherein R$^o$ represents hydrogen or R$^1$, and R$^1$ represents alkyl of C$_1$–C$_6$, 2,2,2-trichloroethyl, 2-iodoethyl, tert-alkenyl of C$_5$–C$_7$, tert-alkynyl of C$_5$–C$_7$, benzyl, nitrobenzyl, tetrahydropyranyl, succinimidomethyl, phthalimidomethyl, methoxybenzyl, dimethoxybenzyl, cyanomethyl, nitrophenyl, dinitrophenyl, 2,4,6-trinitrophenyl, bis(p-methoxyphenyl)methyl, triphenylmethyl, diphenylmethyl, benzyloxymethyl, loweralkanoyloxymethyl of C$_3$–C$_6$, loweralkanoyl of C$_2$–C$_4$, phenacyl, or radical of the formula

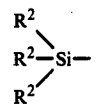

wherein each R$^2$ independently represents loweralkyl of C$_1$–C$_4$ or halo selected from the group consisting of bromo, chloro, fluoro, and iodo, subject to the limitation that at least one R$^2$ represents loweralkyl as defined; and R$^3$ represents amino or an acylamido group where the acyl group is:

alkanoyl of C$_1$–C$_4$,
aroyl of C$_6$–C$_{12}$,
alkoxycarbonyl of C$_1$–C$_4$,
benzyloxycarbonyl,
cycloalkoxycarbonyl of C$_5$–C$_6$,
aryloxycarbonyl of C$_6$–C$_{12}$,
one of the above groups substituted with from one to three groups, each selected from the group consisting of halo, nitro, loweralkoxy of C$_1$–C$_4$, cyano, and, in the instance of aroyl and aryloxy, by loweralkyl of C$_1$–C$_4$, or phthaloyl, subject to the limitation that at least one of the following exists: (1) R$^o$ represents R$^1$; or (2) R$^3$ represents acylamido as defined.

2. The compound of claim 1 which is 7-(5-phthalimido-5-carboxyvaleramido)-3-carbamoyloxymethyl-3-cephem-4-carboxylic acid.

3. The compound of claim 1 which is 7-(5-phthalimido-5-carboxyvaleramido)-3-carbamoyloxymethyl-3-cephem-4-carboxylic acid dimethyl ester.

4. The compound of claim 1 which is 7-(5-(chloroacetamido)-5-carboxyvaleramido)-3-carbamoyloxymethyl-3-cephem-4-carboxylic acid.

5. The compound of claim 1 which is 7-(5-(chloroacetamido)-5-carboxyvaleramido)-3-carbamoyloxymethyl-3-cephem-4-carboxylic acid dimethyl ester.

* * * * *